(12) United States Patent
Panarello et al.

(10) Patent No.: US 11,571,534 B2
(45) Date of Patent: Feb. 7, 2023

(54) POWER SUPPLY FOR RESPIRATORY THERAPY DEVICE

(71) Applicant: ResMed Pty Ltd, Bella Vista (AU)

(72) Inventors: Adam Panarello, Sydney (AU); David Paul Boehm, Sydney (AU); Adrian Ashley Vos, Sydney (AU); Siyin Wong, Sydney (AU)

(73) Assignee: ResMed Pty Ltd

( * ) Notice: Subject to any disclaimer, the term of this patent is extended or adjusted under 35 U.S.C. 154(b) by 542 days.

(21) Appl. No.: 16/094,509

(22) PCT Filed: May 11, 2017

(86) PCT No.: PCT/AU2017/050429
§ 371 (c)(1),
(2) Date: Oct. 18, 2018

(87) PCT Pub. No.: WO2017/193168
PCT Pub. Date: Nov. 16, 2017

(65) Prior Publication Data
US 2019/0117919 A1 Apr. 25, 2019

Related U.S. Application Data

(60) Provisional application No. 62/334,600, filed on May 11, 2016.

(51) Int. Cl.
*A61M 16/00* (2006.01)
*H02J 7/00* (2006.01)
(Continued)

(52) U.S. Cl.
CPC ........ *A61M 16/0003* (2014.02); *A61M 16/00* (2013.01); *H02J 7/0068* (2013.01);
(Continued)

(58) Field of Classification Search
CPC .......... A61M 16/0057; A61M 16/0066; A61M 16/0069; H02J 9/00; H02J 9/005;
(Continued)

(56) References Cited

U.S. PATENT DOCUMENTS 4,284,849 A * 8/1981 Anderson ............... H04M 11/04
379/110.01
4,466,433 A * 8/1984 Robbins ............... A61M 16/021
128/202.22
(Continued)

FOREIGN PATENT DOCUMENTS

CN 1832294 A 9/2006
CN 201752079 U 2/2011
(Continued)

OTHER PUBLICATIONS

Chinese Office Action dated Aug. 20, 2020 for Chinese Patent Application No. 2017800293945.
(Continued)

*Primary Examiner* — Kathryn E Ditmer
(74) *Attorney, Agent, or Firm* — Botos Churchill IP Law LLP

(57) ABSTRACT

A respiratory therapy device generates a flow of breathable gas for therapy. The apparatus may include a flow generator in a housing to generate the breathable gas flow. The flow generator may have an operating voltage for such operations. The device may include a battery pack that is engageable with the housing. The battery pack may be configured to power the flow generator and may include a stand-by circuit configured to switch between stand-by and operating modes. The stand-by circuit may be configured to provide a stand-by operations voltage while in the stand-by mode that is less than an operating voltage of the flow generator and may be configured to detect current demand of the flow generator with the stand-by operations voltage while in (Continued)

stand-by mode such as for enabling an increase voltage from the battery pack to produce the operating voltage in the operating mode for the flow generator.

30 Claims, 9 Drawing Sheets

(51) Int. Cl.
  *H02J 9/00* (2006.01)
  *H02J 9/06* (2006.01)
  *H01M 10/42* (2006.01)
(52) U.S. Cl.
  CPC .............. *H02J 9/005* (2013.01); *H02J 9/061* (2013.01); *A61M 2205/8206* (2013.01); *A61M 2205/8237* (2013.01); *H01M 10/4257* (2013.01); *H02J 7/00302* (2020.01); *H02J 7/00306* (2020.01); *H02J 2207/20* (2020.01)
(58) Field of Classification Search
  CPC ........ H02J 9/007; H02J 7/0013; H02J 7/0029; H02J 7/0068; H02J 7/007; H02J 7/0078; H01M 10/4257
  See application file for complete search history.

(56) References Cited

U.S. PATENT DOCUMENTS

| | | | |
|---|---|---|---|
| 5,341,085 A | 8/1994 | Ettes | |
| 5,503,146 A | 4/1996 | Froehlich et al. | |
| 5,522,856 A * | 6/1996 | Reineman | A61N 1/3706 607/9 |
| 5,628,216 A * | 5/1997 | Qureshi | E05B 47/0012 292/201 |
| 5,975,081 A * | 11/1999 | Hood | A61G 1/00 128/845 |
| 7,956,591 B2 * | 6/2011 | Terlizzi | H02M 1/36 323/282 |
| 8,274,269 B2 | 9/2012 | Kim et al. | |
| 8,581,552 B2 | 11/2013 | Bucur et al. | |
| 2005/0077878 A1 * | 4/2005 | Carrier | H01M 10/441 320/134 |
| 2006/0197498 A1 | 9/2006 | Niculae et al. | |
| 2009/0153124 A1 | 6/2009 | Ishii | |
| 2011/0162647 A1 * | 7/2011 | Huby | A61M 16/1095 128/203.14 |
| 2014/0225620 A1 * | 8/2014 | Campbell | H04Q 9/00 324/426 |
| 2015/0120067 A1 | 4/2015 | Wing et al. | |
| 2017/0229860 A1 * | 8/2017 | Vakilian | H05B 47/18 |
| 2017/0308152 A1 * | 10/2017 | Trichy | G06F 13/4022 |
| 2018/0175649 A1 * | 6/2018 | Cyprowski | H01M 10/44 |

FOREIGN PATENT DOCUMENTS

| | | | |
|---|---|---|---|
| CN | 102209569 A | 10/2011 | |
| EP | 2750262 A1 * | 7/2014 | .............. H02J 9/061 |
| EP | 2750262 A1 | 7/2014 | |
| JP | 2013537065 A | 9/2013 | |
| WO | 2010084444 A2 | 7/2010 | |
| WO | 2012033839 A2 | 3/2012 | |

OTHER PUBLICATIONS

PCT International Search Report dated Jul. 28, 2017.
Human Design Medical, "Powershell Getting Started Guide", Nov. 4, 2013., 2013.
Human Design Medical, LLC, "Z1 CPAP System User Guide", 2015., 2015.
JP Office Action dated Apr. 27, 2021, JP Patent Application No. 2018-559244.
Notification of Second Office Action issued in CN application No. 2017800293945 dated May 7, 2021.

* cited by examiner

POWER SUPPLY FOR RESPIRATORY THERAPY DEVICE

1 CROSS-REFERENCES TO RELATED APPLICATIONS

The present application is a national phase entry under 35 U.S.C. § 371 of International Application No. PCT/AU2017/050429 filed May 11, 2017, published in English, which claims priority from U.S. Provisional Patent Application No. 62/334,600 filed May 11, 2016, all of which are incorporated herein by reference.

2 FIELD OF THE TECHNOLOGY

The present technology relates to power supplies for respiratory devices or apparatus. For example, the present technology may concern power devices or apparatus for efficiently powering respiratory devices in the event the respiratory device is disconnected from mains power or the mains power fails. The present technology also relates to the minimizing the power drawn from the power devices or apparatus when the respiratory devices are not in use.

3 BACKGROUND OF THE TECHNOLOGY

Respiratory devices, such as positive airway pressure (PAP) devices, or ventilators have been implemented to provide various therapies such as the following.

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Such positive airway pressure may be automatically adjusted to different levels upon detection of different sleep disordered breathing events. Similarly, pressures may be modified in synchrony with patient respiration, such as by providing higher pressure(s) during inspiration and lower pressure(s) during expiration for patient breathing comfort.

Non-invasive ventilation (NW) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (W) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

One example PAP device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

A typical PAP system may include a PAP Device, such as a ventilator, an air circuit, a humidifier, a patient interface, and data management.

Examples of respiratory apparatuses include ResMed's S9 AutoSet™ PAP device and ResMed's Stellar™ 150 ventilator. PAP devices or ventilators typically comprise a flow generator, such as a motor-driven blower or a compressed gas reservoir, and are configured to supply a flow of air or other breathable gases to the airway of a patient. In some cases, the flow of air or other breathable gases may be supplied to the airway of the patient at positive pressure. The outlet of the PAP device or the ventilator is connected via an air circuit to a patient interface such as those described above.

Respiratory therapy systems (e.g. ventilators or PAP systems) typically include a respiratory therapy device, an inlet filter, a patient interface, an air circuit connecting the respiratory therapy device to the patient interface, various sensors and a microprocessor-based controller. The patient interface may include a mask or a tracheostomy tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the respiratory therapy device may also include a valve capable of discharging generated air to atmosphere as a means for altering the pressure delivered to the patient as an alternative to motor speed control. The sensors may measure, amongst other things, any of motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

Respiratory devices, or respiratory therapy devices, such as positive airway pressure (PAP) devices or high airflow treatment devices that generate airflow to be directed at patient upper airways, may continually draw power from a consistent power source during operation. Such consistent power sources typically include mains power, such as is found at alternating current (AC) outlets typically found within residences, businesses, and hospitals. However, there are times when mains power is unavailable. For example, mains power may be unavailable when there is a power failure or when a user of the respiratory device is not near an AC outlet.

It may be desirable to develop respiratory devices, such as any of the therapy devices described herein to have a greater degree of portability.

4 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

Some versions of the present technology include a respiratory therapy device to generate a flow of breathable gas to a patient. The device may include a housing. The device may include a flow generator, such as a blower, in the housing to generate the flow of breathable gas. The flow generator may have an operating voltage. The device may include a battery pack engageable with the housing. The battery pack may be configured to power the flow generator. The battery pack may include a stand-by circuit configured to switch between a stand-by mode and an operating mode.

The stand-by circuit may be configured to provide a stand-by operations voltage while in the stand-by mode that is less than an operating voltage of the flow generator. The stand-by circuit may be configured to detect current demand of the flow generator with the stand-by operations voltage while in stand-by mode. The flow generator may further include a current control circuit and a switch, the current control circuit may provide a controlled current upon activation of the switch.

The battery pack may further include a converter to convert a voltage of the battery pack to an operating voltage of the flow generator. The stand-by circuit may be configured to enable the converter upon detection of the controlled current of the flow generator. The converter may be a direct current to direct current (DC/DC) converter configured to increase voltage of the battery pack to the operating voltage of the flow generator. The stand-by circuit may be configured to enable the converter upon detection of the controlled current from the flow generator that exceeds a predetermined threshold value. The stand-by circuit may be configured to enable the converter upon detection of the controlled current from the flow generator that exceeds a predetermined threshold value for a predetermined period of time.

The battery pack may further include a microprocessor. The stand-by circuit may further include a voltage window detector to detect current demand of the flow generator with the stand-by operations voltage while in stand-by mode. The stand-by circuit may be configured to provide the microprocessor with an internal power signal to activate the microprocessor. The stand-by circuit may be configured to provide the microprocessor with an internal power signal to activate the microprocessor to evaluate the detected current demand before activation of the operating mode. In some cases, the microprocessor, upon activation, may determine whether the controlled current from the flow generator exceeds the predetermined threshold value for a predetermined time period, and upon so determining the controlled current exceeds the predetermined threshold value for the predetermined time period, it may activate the converter for the operating mode. In some cases, the microprocessor, upon activation, may determine whether the controlled current from the flow generator exceeds the predetermined threshold value for a predetermined time period, and upon so determining the controlled current does not exceed the predetermined threshold value for the predetermined time period, it may trigger deactivation of the microprocessor.

Optionally, the stand-by circuit may include a high side current mirror circuit that provides the detected current demand to the voltage window detector. In some versions, the flow generator may include an under-voltage lock-out circuit configured to disable the flow generator when the battery pack generates the stand-by operations voltage at an input to the under-voltage lock-out circuit. The under-voltage lock-out circuit may be configured to enable the flow generator when the battery pack generates a higher voltage than the stand-by operations voltage at the input to the under-voltage lock-out circuit. The flow generator may include a controller configured to control the flow generator to generate a positive airway pressure therapy.

Some versions of the present technology may include a battery pack for a respiratory therapy device that generates a flow of breathable gas to a patient. The battery pack may include a battery housing for insertion into a flow generator housing. The battery pack may include a cell within the battery housing for producing a voltage. The battery pack may include a converter to convert the voltage from the cell to an operating voltage for the respiratory therapy device. The battery pack may include a output connector of the battery pack configured to provide the operating voltage to an input connector of the flow generator. The battery pack may include a stand-by circuit coupled to the battery pack.

In some versions, the stand-by circuit of the battery pack may be configured with a stand-by mode in which the stand-by circuit provides a stand-by operations voltage to the output connector that is less than the operating voltage of the flow generator. The stand-by circuit may be configured in the stand-by mode to detect current demand of the flow generator at the output connector with the stand-by operations voltage. The stand-by circuit may be configured to disable the converter in the stand-by mode. The stand-by circuit may be configured to enable the converter upon detection of a controlled current at the output connector of the flow generator with the stand-by operations voltage. The converter may be a direct current to direct current (DC/DC) converter configured to increase the voltage of the battery pack to the operating voltage of the flow generator. The stand-by circuit may be configured to enable the converter upon detection of a controlled current at the output connector that exceeds a predetermined threshold value. The stand-by circuit may be configured to enable the converter upon detection of a controlled current at the output connector that exceeds a predetermined threshold value for a predetermined period of time. The stand-by circuit may include a high side current mirror circuit.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

5 BRIEF DESCRIPTION OF THE DRAWINGS

The present technology is illustrated by way of example, and not by way of limitation, in the figures of the accompanying drawings, in which like reference numerals refer to similar elements including:

6 DETAILED DESCRIPTION

6.1 Overview

Figure 1A:
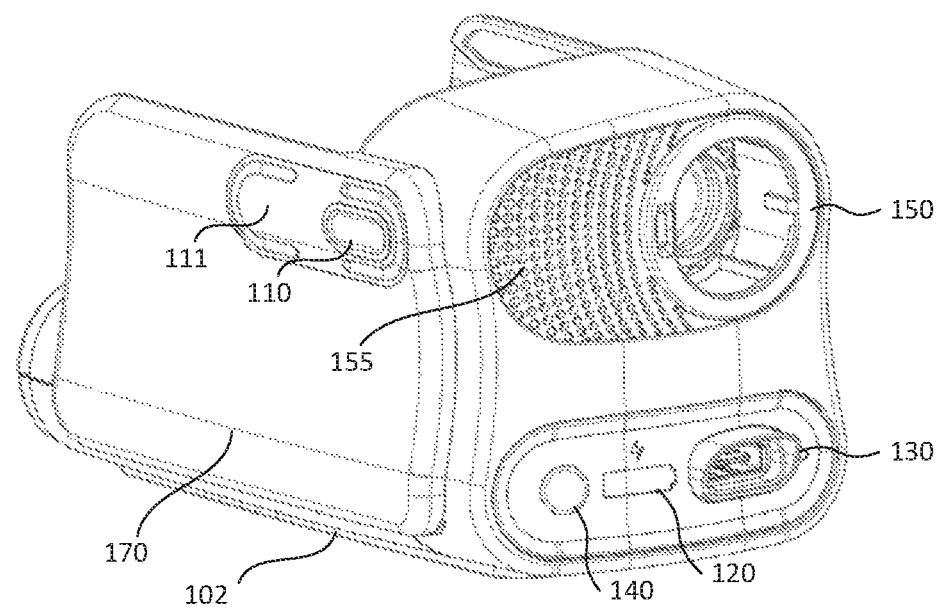
FIG. 1A shows a front view of a battery, in accordance with one form of the present technology.

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

With the advent of smaller respiratory therapy devices (e.g., PAP devices) users may have a desire for autonomy that may be associated with taking their devices away from mains power sources, or other external power sources, such as a DC power supply. In this regard, PAP devices, for example, may be designed to be portable to permit mobility within a residence, business, hospital, or elsewhere. For example, users may desire to use their respiratory devices in airplanes, cars, campers, etc., or other areas where no AC outlets are available or are inconveniently located, or where mains power is unavailable.

Battery packs may be used to provide an alternative and/or backup power source to respiratory therapy devices such as PAP devices. In this regard, the respiratory therapy devices may, for example, be configured to operate at voltages of around 24V, or more or less. However, high-capacity, mass-manufactured battery cells, which provide sufficient energy to power such devices, are most readily available in predetermined voltages (e.g., 4V). Deviation from these predetermined voltages may result in increased cost and/or lowered power capacity.

To achieve the voltage necessary to operate a respiratory therapy device (including a blower included therein as well as any other components thereof), such as around 24V, or more or less, multiple battery cells may be placed in series within a battery pack. However, with each additional battery cell placed in series, an increase in the bulk and size of the battery pack may result. Further, the amount of heat output by the battery pack may also increase with each additional battery cell, necessitating the need for the battery pack to have a larger surface area to allow for adequate heat dissipation. Moreover, the voltage of battery cells can vary as the stored charge is lost or depleted, and the respiratory therapy device is designed to run at a particular/desired voltage. Thus, it is desirable to provide a power source to ensure/regulate the desired voltage.

To achieve a regulated output voltage, with high conversion efficiency, a direct current to direct current (DC/DC) converter may be implemented. For example, a battery pack with a nominal, lower voltage (e.g., about 12V) may be connected to a DC/DC converter. The DC/DC converter, which may optionally be integrated within the battery pack or within the respiratory therapy device (e.g., in its housing), may convert the power signal from the battery cells at a lower voltage (e.g., around 12V) up to the higher operating voltage of the respiratory therapy device (e.g., PAP device), such as at about 24V, or more or less. However, unless switched off, the energy consumption of the DC/DC converter is such that if left on, it may noticeably decrease the shelf life of the battery pack, such as between therapy sessions, or at a point of sale, for example. On the other hand, if the output DC/DC converter is switched off, the user may not be able to switch on the PAP device when activating its 'on' button, as the power may not available to the PAP device. Thus the user may have to remember to switch the DC/DC converter between its 'on' and 'off' states every time, to the detriment of the user's convenience.

Thus, in some versions of the present technology, a power source may be implemented for portable operation of a respiratory therapy device without being connected to a mains power. Some versions may include a power sub-system that may operate at a different voltage to that of the flow generator of the respiratory therapy device (e.g., PAP device). The power sub-system may include a battery pack for the respiratory therapy device configured to enter into a 'stand-by' mode, such as by inclusion of stand-by mode circuitry. The stand-by mode circuitry may allow a DC/DC converter in the battery pack to be switched 'off' until receiving the 'on' signal from the respiratory therapy device controller. The stand-by mode circuitry may be configured so that when in the 'stand-by' mode, little to no energy is consumed from the battery pack (i.e., from the battery cells). The DC/DC converter when switched "on" may, for example, convert a lower voltage (e.g., a battery cell output voltage) to a higher operational voltage needed for therapy operations of the respiratory therapy device.

Figure 1B:
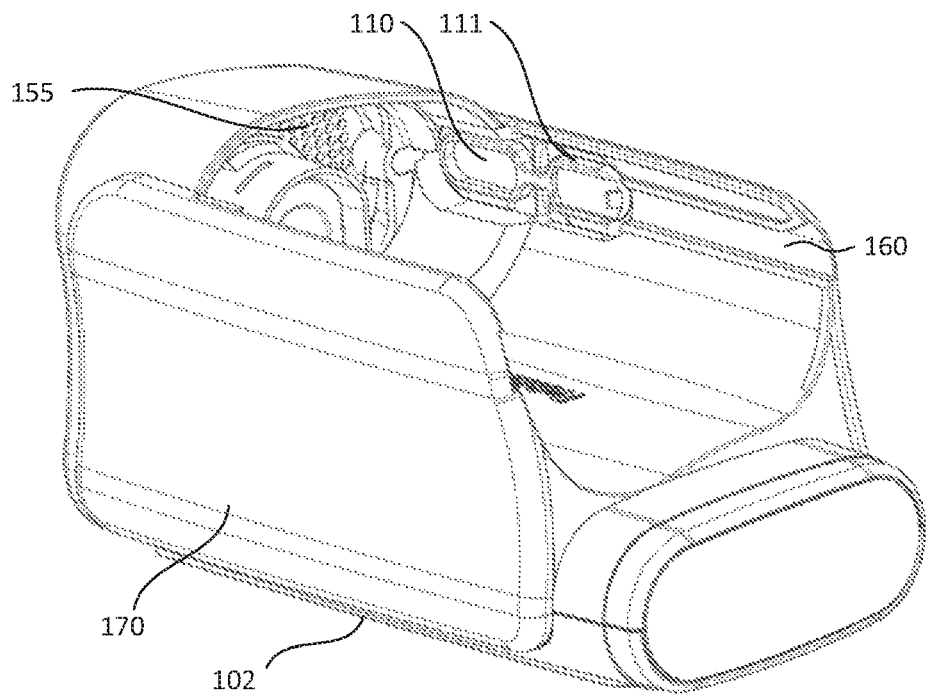
FIG. 1B shows a back view of a battery, in accordance with one form of the present technology.

The battery pack may be configured to power a respiratory therapy device, such as for therapy operations (e.g., treatment pressure generation or airflow production). For example, as shown in FIGS. 1A and 1B, the housing 170 of the battery pack 102 may include a locking mechanism 111, and a guide slot 160 for connecting/inserting a PAP device into the battery pack. A release button 110 may be used to release the PAP device from the battery pack 102. In addition, the housing 170 may also include a power connector 130 (e.g., AC or DC connector) for the battery pack, which may connect to an external power source, such as a mains power source. Other components of the battery pack 102 may include a battery life indicator actuator 140 for starting operation of the battery life indicator 120, wherein the battery life indicator 120 indicates the amount of charge left within the battery pack 102. The battery pack may also be comprised of an air outlet 150 for delivering respiratory therapy, such as pressurized air or other gas via a patient interface (e.g., full-face mask, nasal pillows, nasal cannula, nasal mask etc.), to a user of the inserted respiratory therapy device from its internal flow generator (e.g., a servo-controller blower, comprising a motor and an impeller within a housing, such as a volute). The battery pack 102 may include a mesh flow generator inlet 155, such as with a filter, that is configured to filter air drawn into the flow generator of the PAP device 202 through the housing of the battery pack 102.

Figure 2A:
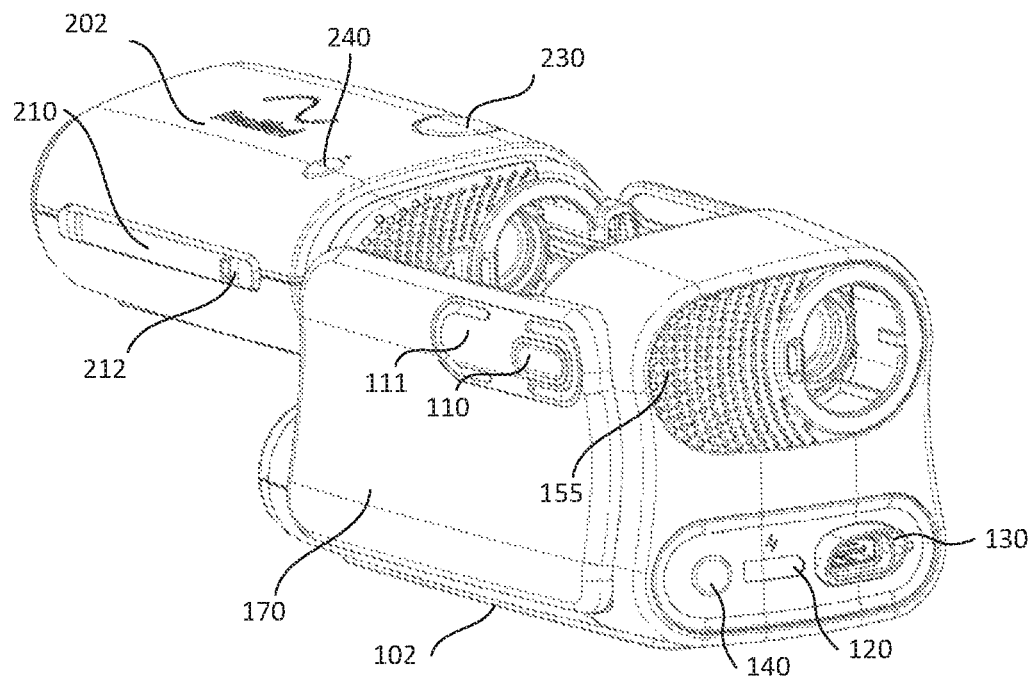
FIG. 2A shows a front view of a battery, and a respiratory therapy device, such as a PAP device, in accordance with one form of the present technology.
Figure 2B:
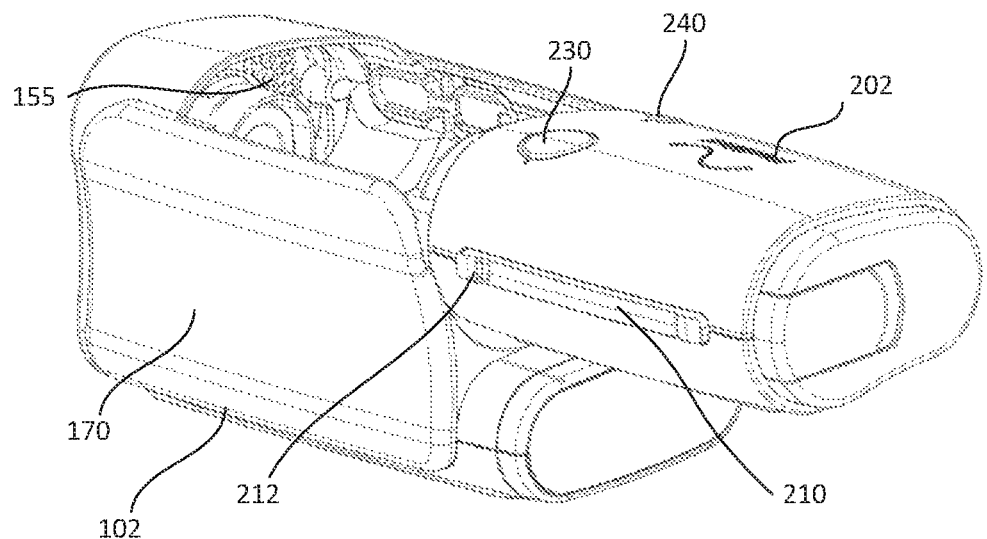
FIG. 2B shows a back view of a battery, and a respiratory therapy device, such as a PAP device, in accordance with one form of the present technology.
Figure 3A:
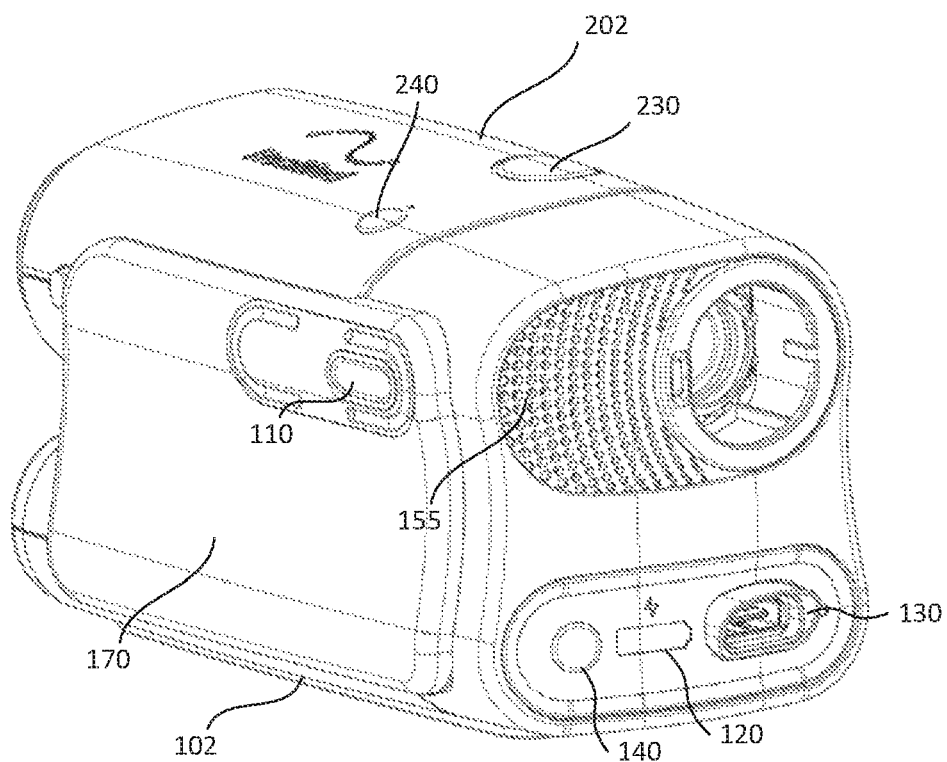
FIG. 3A shows a front view of a battery with a respiratory therapy device, such as a PAP device, attached in accordance with one form of the present technology.
Figure 3B:
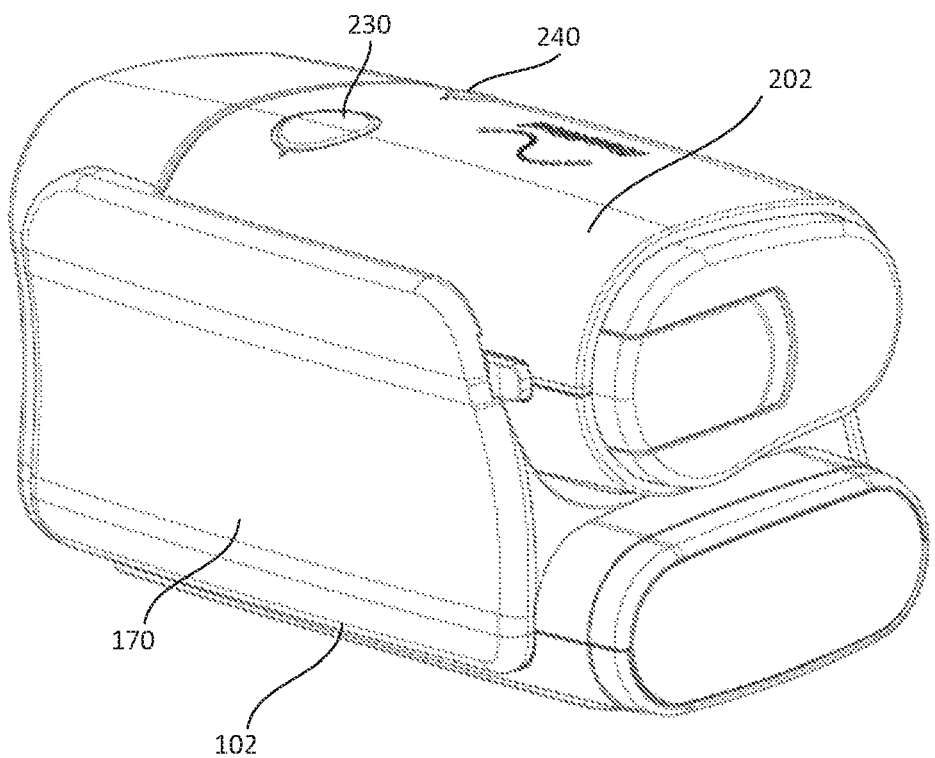
FIG. 3B shows a back view of a battery with a respiratory therapy device, such as a PAP device, attached in accordance with one form of the present technology.

The PAP device may be configured to removeably connect to or insert within the housing of the battery pack 102. For example, as shown in FIGS. 2A and 2B, the PAP device 202 may include a guide rail 210, or rails as there may be one on each side, which may be inserted into the guide slot 160, or slots as there may be one on each side to complement the rails, of the battery pack 102, as shown in FIGS. 1A and 1B. The guide rail 210, in conjunction with the guide slot 160, may enable an easy and accurate connection/alignment between the electrical couplers of the battery pack 102 and the PAP device 202. In this regard the guide rail 210 may be inserted into guide slot 160. The guide rail 210 may then slide down the guide slot 160, causing the PAP device 202 to be positioned in a predetermined configuration within the housing 170 of the battery pack 102, as shown in FIGS. 3A and 3B. The PAP device 202 may also include a connector 212 which may latch, or otherwise attach, into the locking mechanism 111. As further shown in FIGS. 3A and 3B, the PAP device 202 may fit compactly within the housing 170 when the components are locked or otherwise attached together. The connection between the battery pack 102 and the PAP device 202 may be maintained until the locking mechanism 111 is released by action of release button 110.

The PAP device 202 may be include a blower, an inlet filter, various sensors and a microprocessor-based controller and may comprise an outlet connectible to a patient interface via an air circuit. Power to the PAP device 202 may be controlled by power a switch 230. In this regard, a user of the PAP device may switch the PAP device to an 'on' and 'off' state by activating and deactivating its power button with switch 230, respectively. As described in greater detail herein, the power button or switch 230 may switch a DC/DC converter of the battery pack 102 between an 'on' and 'off' state.

The PAP device may communicate with other computing devices. In this regard, the PAP device may include a wireless pairing button 240, for connecting the PAP device to other computing devices, such as tablets, smartphones, computers, etc., through a Bluetooth, or other such wireless communication protocols. Optionally, such communications may be implemented with a wired connection, such as with wires of the power connector or other data wire connection, for which a pairing button may not be necessary. For example, wired connections may be implemented for communication between system components (e.g., battery-to-PAP device and/or PAP device-to-humidifier, etc.) The PAP device may provide status updates to the other computing device(s). The status updates may include a power level report of the battery pack 102, usage statistics of the PAP device 202, including data indicating a therapy data such as the flow rate or pressure, and data indicating compliance data such as time usage of the PAP device, and other such usage data. Such communications may permit setting of operational/control parameters of the PAP device (e.g., pressure and/or flow settings) without a built in physical user interface in the PAP device or battery pack. Thus, the PAP device may omit a display (e.g., LED display) and more extensive input control buttons (e.g., keyboard) to promote a smaller more portable size.

While a PAP device is illustrated in the figures, other respiratory therapy devices as described herein may be similarly implemented such as a portable ventilatory support device.

6.2 Power Configurations

Figure 4:
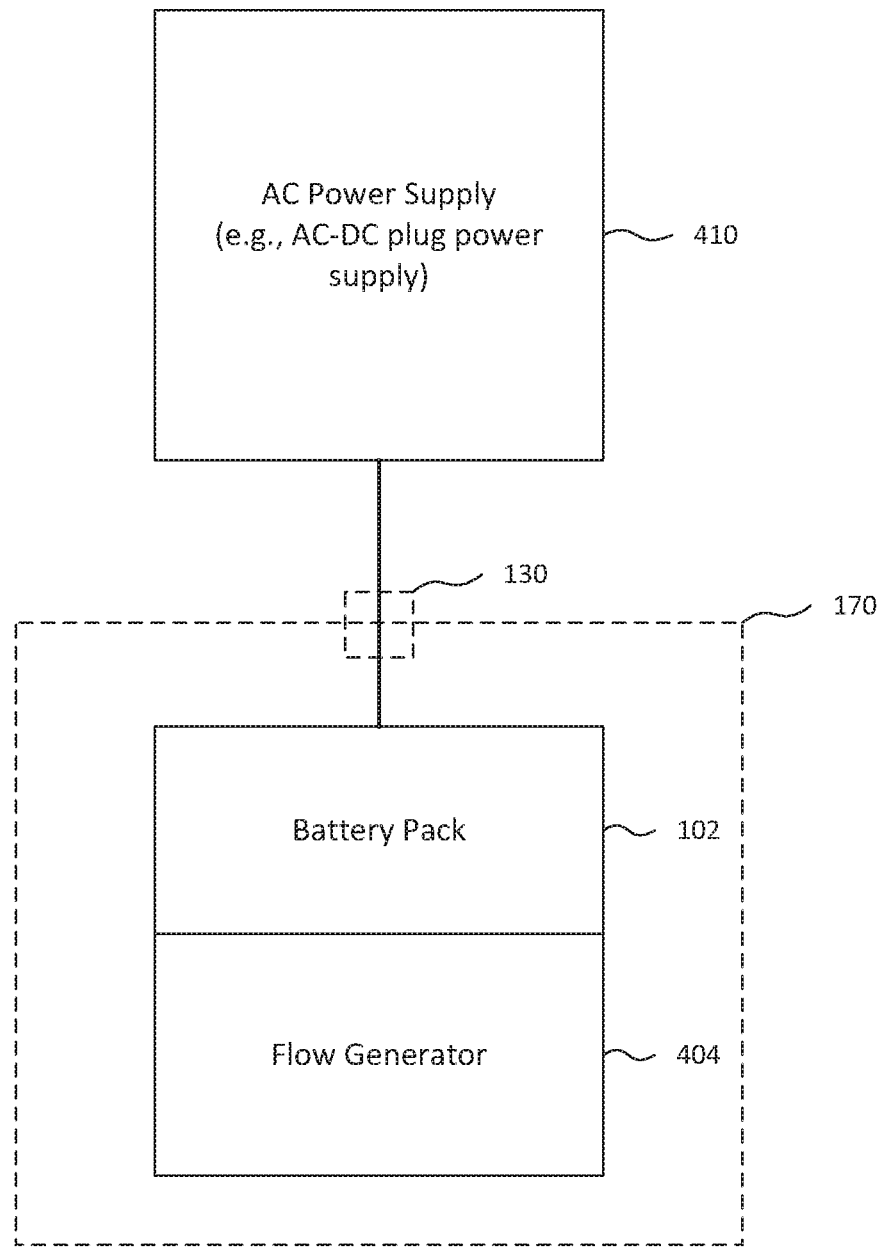
FIG. 4 shows a AC power configuration of a respiratory therapy device, such as a PAP device, in accordance with one form of the present technology.

The respiratory therapy device may be configured to be powered by any of a plurality of different types of power sources. For example, as shown in FIG. 4, an AC power supply 410 (e.g., mains power supply) may optionally be connected to the components of the PAP device 202 (e.g., the flow generator 404) through the electrical couplers via an power connector 130 or an integrated power supply cable/plug of the battery pack or its housing. In this regard, the AC power supply 410 (mains) may be connected through the power connector 130 to the flow generator 404 and/or to the battery pack 102 using, for example, a AC-DC power converter plug pack power supply. Thus, the AC power supply 410 may connect through an AC/DC adapter (not shown), to convert the AC power signal to a DC power signal. For example, a 120 volt (V) or 240 volt (V) alternating current (AC) power signal generated by a mains power source may be received and converted by the AC/DC adapter into a 24V direct current (DC) signal or 12V DC signal, or more or less. The converted DC signal may be output from the AC/DC adapter directly to the flow generator 404, and/or to the battery pack 102, such as for charging the battery pack.

Figure 5:
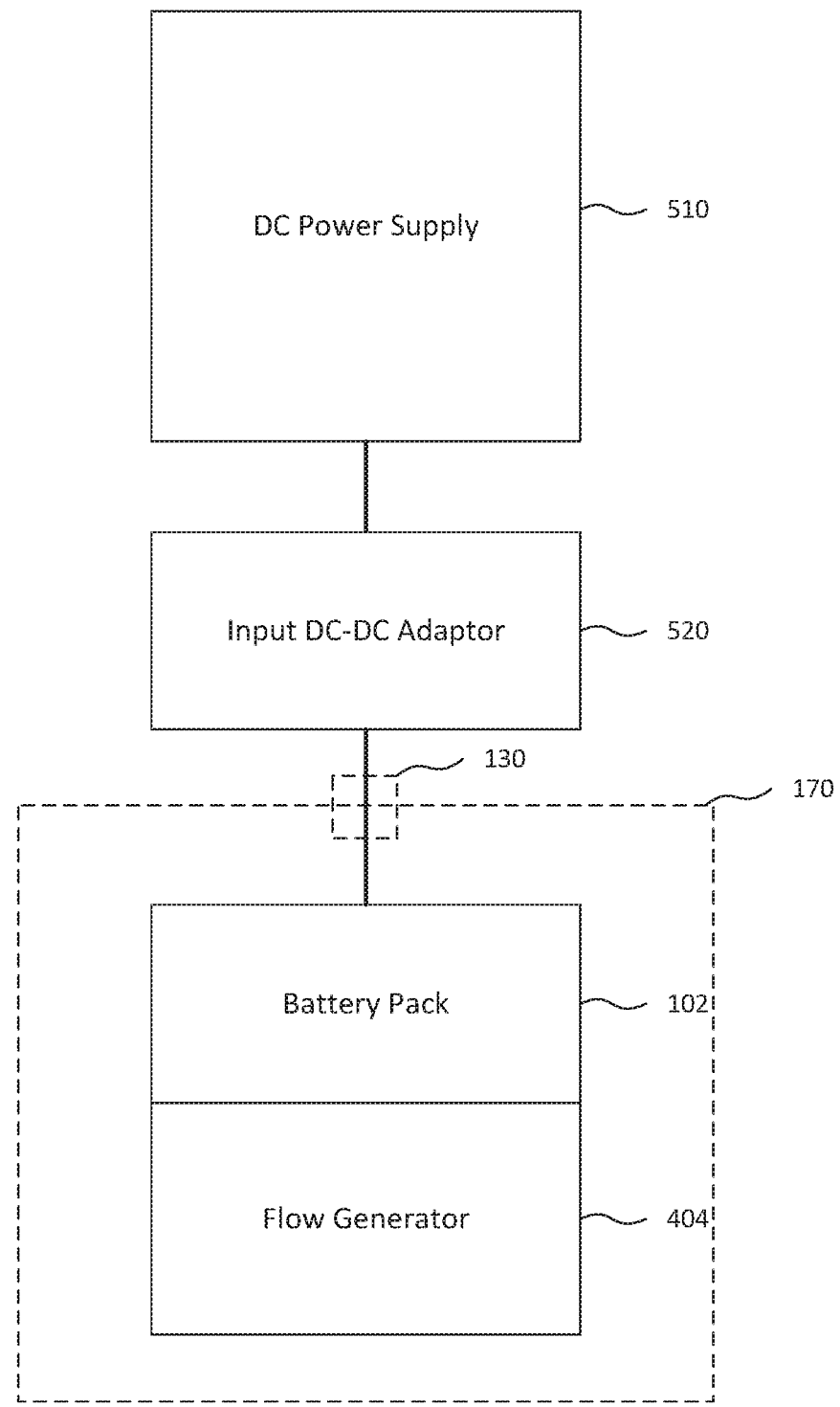
FIG. 5 shows a DC power configuration of a respiratory therapy device, such as a PAP device, in accordance with one form of the present technology.

The respiratory therapy device may also be powered by a DC power supply 510, as shown in FIG. 5. As with the connection to the AC power supply 410, described above, the DC Power supply 510 may be connected to the power connector 130 of the battery pack 102, as shown in FIG. 1A, or directly to the PAP device 202. However, to assure that the correct voltage is delivered to the respiratory therapy device, such as 24V, or more or less, an input DC/DC converter 520 may be included in-line or between the DC power supply 510 and the components of the PAP device 202 (e.g., the flow generator 404 and the battery pack 102). The input DC/DC converter 520 may be configured to convert the voltage of the power signal received from the DC power supply 510 to a voltage that may be appropriate for operation of the respiratory therapy device and/or charging of the battery pack. In some versions, the DC power supply 510 may be a supply that provides between 6V and 24V, or more or less, such as 12V or 24V, and the input DC/DC converter 520 may increase that voltage to the operative voltage of the PAP device or battery pack, such as 24V, or more or less.

In the event of a mains power failure, or unavailability, the respiratory therapy device may be powered for therapy operation by the battery pack 102. For example, when the AC power supply 410 or DC power supply is disconnected from the battery pack 102, the flow generator 404 of the PAP device 202 may draw power from the battery pack 102. In some embodiments the conversion from mains power to battery power may be automatically implemented. In this regard, the battery pack 102 and/or PAP device 202 may include circuit components that automatically detect a mains power loss. Upon detecting a mains power loss, the PAP device 202 may automatically begin to draw power from the battery pack 102. In other versions, a user of the respiratory therapy device may manually switch the device to draw power from the battery, such as the battery pack 102.

The battery pack may be charged while the respiratory therapy device is connected to an external power source, such as an AC power supply or a DC power supply. In this regard, when the battery pack 102 is connected to the PAP device 202, as shown in FIG. 3, the power required for running the respiratory therapy device to provide therapy can take priority. For example, the power required for running the flow generator 404 of the PAP device 202 may take priority over charging the battery pack 102. Therefore, battery charging may pause, or the charging rate may be reduced, during times of high power draw from the external power supply by the PAP device 202. In some versions, the battery pack 102 may be connectable directly to an external power source to be charged. For example, the battery pack 102 may be configured to be couple to an external power source for charging when it is not connected to the flow generator 404 of the PAP device.

6.3 Battery Configuration

Figure 6:
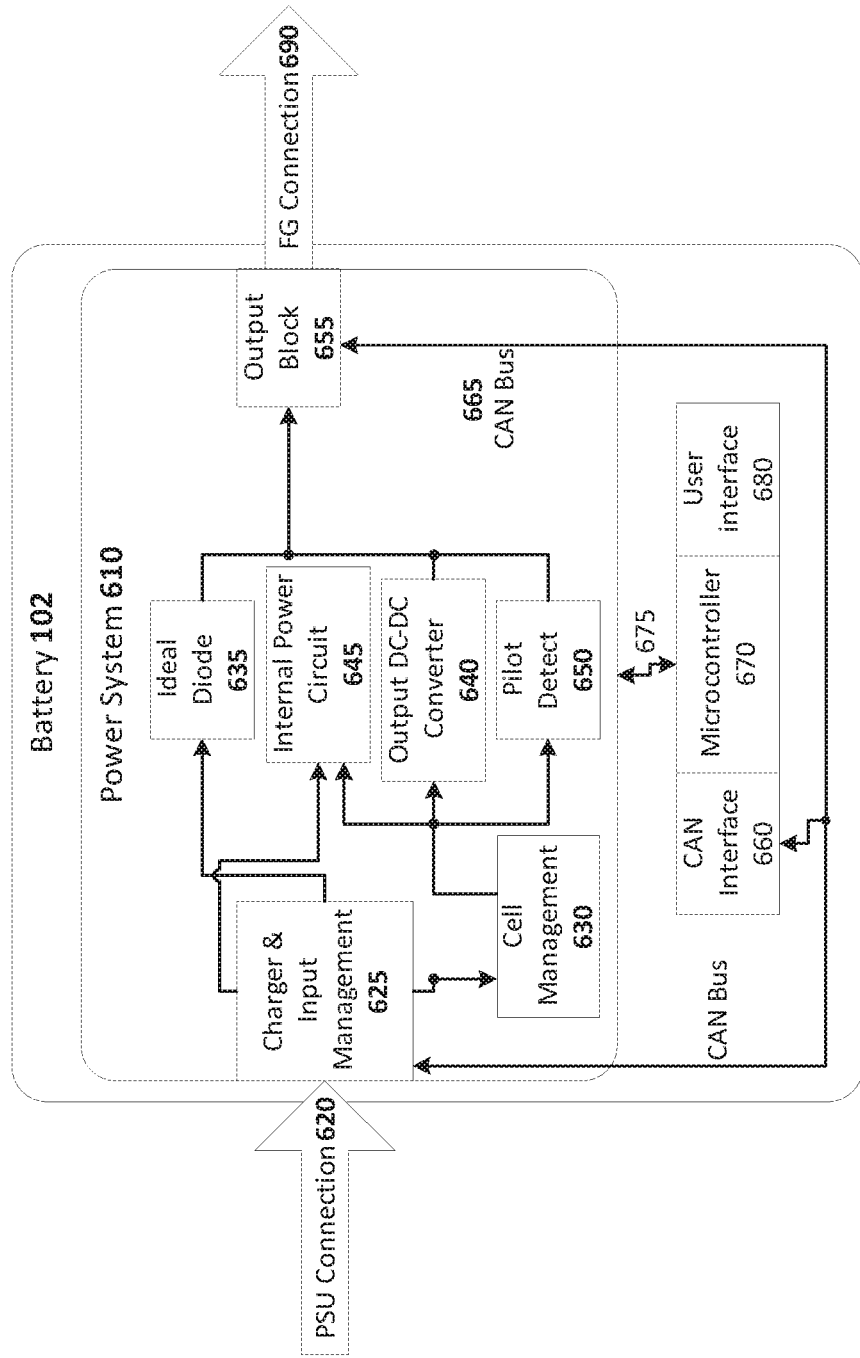
FIG. 6 shows components of a battery in accordance with one form of the present technology.

Components of an example battery pack are illustrated in the diagram of FIG. 6, showing a schematic of a battery 102. As shown in FIG. 6, the battery pack may include a power system 610, interfaces 660, 680, and one or more controllers (e.g., microcontroller 670). Thus, the components of the battery pack, and their respective operations, may be controlled with hardware and/or software. For example, hardware may be implemented to control some functions of the battery such as the charging of cell(s) of the battery pack, measuring the temperature inside of the battery pack casing, providing battery protection functions, and activating the battery (e.g., power on and power off). Software may implement functions for monitoring for alert conditions or errors, monitoring the charge state of cell(s), displaying battery status (i.e., charge amount, battery health, etc.,) activating charging of the battery when a correct power supply type and amount is powering the battery, controlling the charging power limits, and communicating with other system components. The functions performed by the controllers described herein (e.g., microcontroller 670) may also be performed by one or more timers and logic devices, such as a programmable logic device, an application-specific integrated circuit ("ASIC"), or other discrete logic device. The software and hardware functions may be implemented by the modules described below.

The power system 610 of the battery pack 102 may be controlled by a microcontroller 670, which communicates through a controller area network (CAN) interface 660 using a CAN bus. The microcontroller 670 may also communicate through a system management bus (SMB) shown at connection 675. Although not shown, the connection 675 may further include plurality of control and monitoring lines between the microcontroller and the components of the power system 610. The CAN interface 660 may enable the microcontroller 670 to communicate through the CAN bus 665.

Generally, the microcontroller 670 may communicate with internal components of the power system 610 via the SMB. For example, the microcontroller 630 may communicate with an integrated chip (IC) of the cell management module 630 through the SMB. The microcontroller 630 may also communicate with an integrated chip (IC) of the charger and input management module 625 through the SMB. Moreover, the microcontroller 670 may communicate with external components via the CAN bus 665. For example, the microcontroller may communicate with a processor or controller of the flow generator (or a controller of any one or more of a humidifier, production system(s) or other external devices) through the CAN bus 665. The microcontroller 630 may also communicate with an integrated chip (IC) or controller of a power supply (e.g., through the PSU connection) via the CAN bus 665.

For example, the controller of the flow generator may communicate or poll the microcontroller 670, via the CAN bus 665 through the output block 655 such as for determining available battery charge or other power supply operational related information. The microcontroller 670 may then poll or communicate with the one or more components of the power system 610 for such information via the SMB. Upon receiving such information from the SMB, the microcontroller may send the information to the controller of the flow generator to the CAN bus.

Thus, the microcontroller 670 may communicate with the flow generator 404 of the PAP device 202 via the output block 655, which may contain protection circuits for the CAN bus 665. The output block 655 may also include an output connector, filtering components, voltage and current monitoring components. Similarly, microcontroller 670 may communicate with an external power supply component via the charger and input management module 625, which may also include protection circuits for the CAN bus 665.

In some embodiments, the CAN interface 660 and CAN bus 665 may supply power to the microcontroller 670 and/or interface 680.

Thus, the microcontroller 670 may communicate with the battery pack 102 over the system management bus (SMB) at connection 675. In this regard, the microcontroller 670 may receive information regarding the components of the battery and provide instructions to control the functions of the battery over the SMB at connection 675. For example, the microcontroller may receive information, such as the charge level of the battery pack from the cell management module 630 via the SMB at connection 675. The microcontroller may then cause the user interface 680 to display a battery status on a user interface 680 (e.g., battery life indicator 120). The microcontroller 670 may also monitor internal temperature and the condition of the cell(s), mediate (i.e., control the communication between the various modules, such as cell management module 630 and the charger circuits), and control and/or monitor the various other battery components, such as discussed in more detail herein.

The user interface 680 may be configured to provide a user with status updates concerning the battery (e.g., display battery related output) and interact with the battery pack 102 (e.g., input for setting or activating operations of the battery pack). In this regard the user interface may be configured to provide a battery charge status to user (e.g., percent charged or time to full charge) and/or provide an operation status to a user (e.g., time until battery is drained and/or amount of power being drawn from the battery). The user interface 680 may also accept input from a user. Such inputs may affect the operation of the battery such as starting or stopping internal power of the battery on detecting one or more button operation signals (e.g., on or off button activation). In some cases, this user interface may provide visual output to the user concerning the status of the battery charge in response to a button activated by a user.

Thus, in an embodiment of the present technology, the user interface 680 may include one or more input devices in the form of buttons, such as power button (e.g, switch 230) in FIGS. 2A and 2B, switches or dials to allow a person to interact with the device.

Optionally, an additional user interface for the PAP device may also provide buttons, switches or dials, such as physical devices, or software devices, accessible via a touch screen. Such buttons, switches or dials may, in one form, be physically connected to the PAP device 202, or may, in another form, be in wireless communication with a receiver that is in electrical connection to a controller, such as of the PAP device. Such a user interface may be constructed and arranged to allow a person to select a value and/or a menu option such as through wireless communications from a mobile processing device (e.g., smart phone processor running a control application).

The power system 610 of the battery may receive a power signal from a power supply unit (PSU) via a PSU connection 620. In some embodiments the PSU connection 620 may be the power connector 130, as shown in FIG. 1A. The power signal may be processed and conditioned by the power system 610. The conditioned power signal may then be output to a PAP device via a flow generator connection 690. The power system 610 may include an ideal diode 635 to prevent current from flowing in the wrong direction, such as from the output to the input. The power system 610 may include internal rails or internal power nodes (e.g., wired connections), powered by an internal power circuit 645, which provide internal DC power to the various components and modules.

The power signal may be provided from the PSU connection 620 to a charger and input management module 625. The charger and input management module 625 may include one or more integrated circuits, such as IC model number BQ24725 provided by Texas Instruments. These circuits may be configured to monitor and control the charging of the cells of the battery pack 102. In this regard the charger and input management module 625 may monitor the input voltage and current of the power signal, as well as the power signal output to charge the battery cells. Thus, a battery cell charger circuit may have an integrated circuit that communicates with the cell management module 630 through the SMB at connection 675 to control the battery cell charging. In this regard the battery cell charger circuit may provide over/under voltage lockout and monitor and limit the charge current. The monitored power conditions, as well as the state of the battery cell charging may be passed to the microcontroller 670 through the SMB at connection 675. The microcontroller 670 may provide charging instructions to the charger and input management module 625 such as instructions for controlling the voltage and current output to the battery cells.

The charger and input management module 625 may include circuits and circuit components to also provide power conditioning. For example, the charger and input management module 625 may control and/or minimize the conducted noise in the power signal and provide electrostatic discharge and transient protection. The charger and input module 625 may also provide over/under voltage protection such as over/under voltage lockout, perform input blocking under output fault conditions, and/or provide battery cell charging capability. In some embodiments the microcontroller 670 may provide instructions to the charger and input management module 625, such as, instructions controlling the type and amount of power conditioning through the SMB at connection 675.

The battery may also comprise a cell management module 630. The cell management module 630 may control the charging and discharging of the battery cell(s) of the module. For example, the cell management module 630 may include one or more integrated circuits to control the energy storage of the cell(s), provide the power status of the cell(s) (i.e., the cell(s) power balance and charge capacity), provide requests for charge current and voltage, and provide other such cell status information to the microcontroller 670 via the SMB at connection 675. The cell management block 630 provides the instructions regarding charge rate etc. These are passed on by the microcontroller 670 to the charger via SMB. Additionally, the cell management module 630 may store the battery pack's serial number for traceability, lifetime usage data, and end of line test data (i.e., testing after the battery has been manufactured).

The cell management module 630 may also provide primary and secondary cell charge and discharge protection so that the cell(s) remain within safe operational parameters. For example, the one or more integrated circuits of the cell management module 630 may provide charge and discharge protections such as cell parameter monitoring (e.g., over/under voltage protection, over current protection, over/under temperature protection, cell voltage imbalance, etc.). Additionally, the one or more integrated circuits of the cell management module may provide cell protection cut-offs to stop the charging or discharging of the battery cells charge or discharge when predetermined limits are exceeded. In some embodiments the cell management module 630 may permanently disable the charge and discharge when unrecoverable fault conditions are determined. In some versions, the cell management module may include a management IC, such as a Texas Instruments BQ40Z50 and/or a cell over voltage protection IC such as a Texas Instruments BQ294702.

An internal power circuit 645 may supply power to internal circuits within the battery pack 102. In this regard, it provides power to the pilot detect circuit 650 and microcontroller 670. Power may be delivered from the internal power circuit to the internal circuits via the internal DC rails. In some embodiments the internal power circuit 645 may provide low voltage and low power signal supplies. The internal power circuit 645 may implement a low current draw for the 'stand-by' mode in relation to the pilot detect circuit, thereby limiting the amount of power drawn by the battery as discussed in more detail herein.

An output direct current to direct current (DC/DC) converter 640 may be used to convert the nominal voltage of the battery cell(s) to, for example, a regulated higher output voltage. For example, the battery pack's 102 cell(s) may output a 12V output power signal, or more or less, to the output DC/DC converter 640. The output DC/DC converter 640 may then convert the 12V output power signal to the operating voltage of the PAP device, such as a higher output voltage, for example, of about 24V, or more or less. The output power signal may also be regulated by the output DC/DC converter 640 to maintain the output power signal within the operating parameters of the respiratory therapy device, such as 24V±1V.

In some instances the output DC/DC converter 640 may provide regulation status updates to the microcontroller (e.g., through hardware and/or analog to digital conversion (ADC)) and/or user interface via the CAN bus. For example, output DC/DC converter 640 may track the voltage of the output power signal over time, and provide such information to the microcontroller 670, which may optionally be output via user interface 680.

In certain embodiments the output DC/DC converter may provide isolation between the battery cell(s) and other components of the battery pack 102. For example, should the battery cell experience a fault or the battery be placed into a 'stand-by' mode, the output DC/DC converter may assure that power is not sent to the PAP device or other portions of the power system 610.

The battery may also include a pilot detect module 650. The pilot detect module 650, serving as a pilot voltage source, may provide a pilot voltage, such as a high impedance cell voltage to the output block 655. This voltage might not be regulated and may be dependent on the cell voltage. This high impedance voltage source is lower than the intended full output voltage of the battery pack. With this pilot voltage, the pilot detect module 650 is also enabled for detecting when a particular range of current is drawn from the battery cells from the PAP device 202.

The pilot detect module 650 may be implemented to detect a current draw on the pilot voltage source, and start or permit internal power when the current draw surpasses a predetermined threshold or when the current draw is within a desired current range for a certain period of time. As such, the pilot detect module 650 may be used to switch the power sub-system from 'stand-by' mode to an 'on' mode, as described in further detail below.

An output block 655 may be used to manage a connection between the battery pack 102 and the flow generator 404. In this regard the output block 655 may provide a flow generator connection 690 with the output power signal and access to the CAN bus. The output block 655 may also provide output voltage and current monitoring, output fault latch off control, conducted noise control, and electrostatic discharge and transient protection to the battery pack 102 and the PAP device 202. For example, the output block 655 may monitor the voltage and/or current of the output power signal and trigger a disconnection at the flow generator connection 690 when the voltage and/or current of the output power signal surpasses a predetermined threshold value. In another example, the output block 655 may address transient signals and/or conducted noise generated by modules within, and external to, the power system 610 and/or battery pack 102. Optionally, the output block may provide ESD (electrostatic discharge) and/or EMI (electromagnetic interference) protection.

6.4 Stand-by Mode

Some internal circuit components of the battery system may draw power from the cell(s) charge even when the respiratory therapy device is not operational. For example, battery systems that include internal circuits for providing a regulated output voltage higher or lower than the internal cell(s) voltage, such as the output DC/DC converter 640, may generally deplete the cell(s) charge over time as such a converter may continually draw power from the cell(s) even when other systems intended for the battery are not in operation. Thus, in some versions the longevity of the battery cell(s) charge may be improved by not operating/powering many of the internal circuit components of the battery system when the respiratory therapy device is not operational for respiratory use (e.g., providing a therapy to a patient).

Further, for usability purposes, it may be more convenient for the user to operate a respiratory therapy device configured to be powered by actuation of a power button on the body of the respiratory therapy device, such as power button or switch 230 as shown in FIGS. 2A and 2B. As a corollary, having to activate the internal circuits of a connected battery power source and then subsequently power the PAP device 202 may inconvenience the user. Thus, it may also be desirable for an unpowered device, such as the PAP device 202, to activate the battery along with itself, while not drawing any (or very little) power from the batteries cell(s) such as if the device is not activated.

Thus, in some versions, the respiratory therapy device, such as a PAP device 202, may include power components to implement a 'stand-by' mode. For example, a 'stand-by' mode may be implemented with the pilot detect module 650 of the battery pack 102 in conjunction with the microcontroller 670 and/or other components, such as components that may be part of the PAP device 202. In this regard the pilot detect module 650 may form a part of a stand-by circuit within the battery pack 102 and/or PAP device 202. In some embodiments the circuits for the stand-by mode may be integrated into the internal power circuit 645.

The stand-by mode may have a 'stand-by' state (i.e., 'off' state) and an 'on' state (i.e., 'operating' state). In this regard, when the circuit components implementing the stand-by mode are in the 'stand-by' or 'off' state, the battery, such as battery pack 202, is disabled from providing the full operating voltage necessary for operating the therapy or PAP device. The battery pack 102, such as with its cells, may then produce a relatively high impedance stand-by voltage at the output block 655. This stand-by voltage source may be at a lower voltage than the full output power signal that would otherwise be enabled. The lower voltage may be provided to the PAP device 202 via the flow generator connection 690. In some embodiments some or all of the other internal components, such as the output DC/DC converter 640 may be turned 'off' and be provided with no power when the stand-by mode is in the 'stand-by' state. In this regard, power to some or all of the internal DC rails may be reduced and/or turned off. Thus, the 'stand-by' mode may reduce power and reduce battery depletion.

Conversely, when the stand-by circuit is in the 'on' state, the battery pack is enabled for providing the complete/necessary operating output power signal (e.g., 24V, or more or less) for the flow generator 404 or the respiratory therapy device (e.g., PAP device 202). In this regard, when the stand-by circuit is in the 'on' state, the internal components, such as the output DC/DC converter 640 circuit may receive the power necessary to operate from the internal DC rails. In this regard, the power may be generally available to the DC-DC converter but it will not be running when in the standby state.

In some versions of the stand-by circuit, the pilot detect module 650 may be configured to monitor for a particular current range (e.g., a measure of current within a set of thresholds indicative of the desired range) being drawn by the PAP device 202 from the source (e.g., the battery cell(s)). Detection of such a current range may automatically trigger a switch of the state of the stand-by circuit, from 'off' to 'on'. In this regard, while the stand-by circuit is in an 'off' state, the pilot detect module 650 may monitor the battery's output terminals. Due to the high impedance of the stand-by voltage source, the pilot detect module 650 may be able to determine when a relatively small amount of current is drawn from the stand-by voltage source while consuming a relatively small amount of power. Upon detecting the current drawn from the stand-by voltage source surpasses a predetermined threshold and/or the current draw is maintained within the particular range for a certain amount of time, the pilot detect module 650 may switch the system from 'stand-by' mode to an 'on' mode. As previously described, while in 'on' mode the battery pack may provide the full output power signal to the PAP device. In this fashion, operation of the DC/DC converter 640 and the resultant increase in voltage produced from the battery cell(s) may be triggered by demand (e.g., activation) of the flow generator or the PAP device. Thus, the therapy or PAP device may be configured to draw the current range required to switch the stand-by circuit. For example, the respiratory therapy device may include a button (e.g. a power button) that, upon activation, connects a load to draw the current within the required current range (and optionally also switch the respiratory therapy device "on" when the stand-by circuit is in its 'on' state). The same button may also serve to switch the respiratory therapy device on when it is connected to an AC/DC adapter and not to the power supply system.

Figure 7:
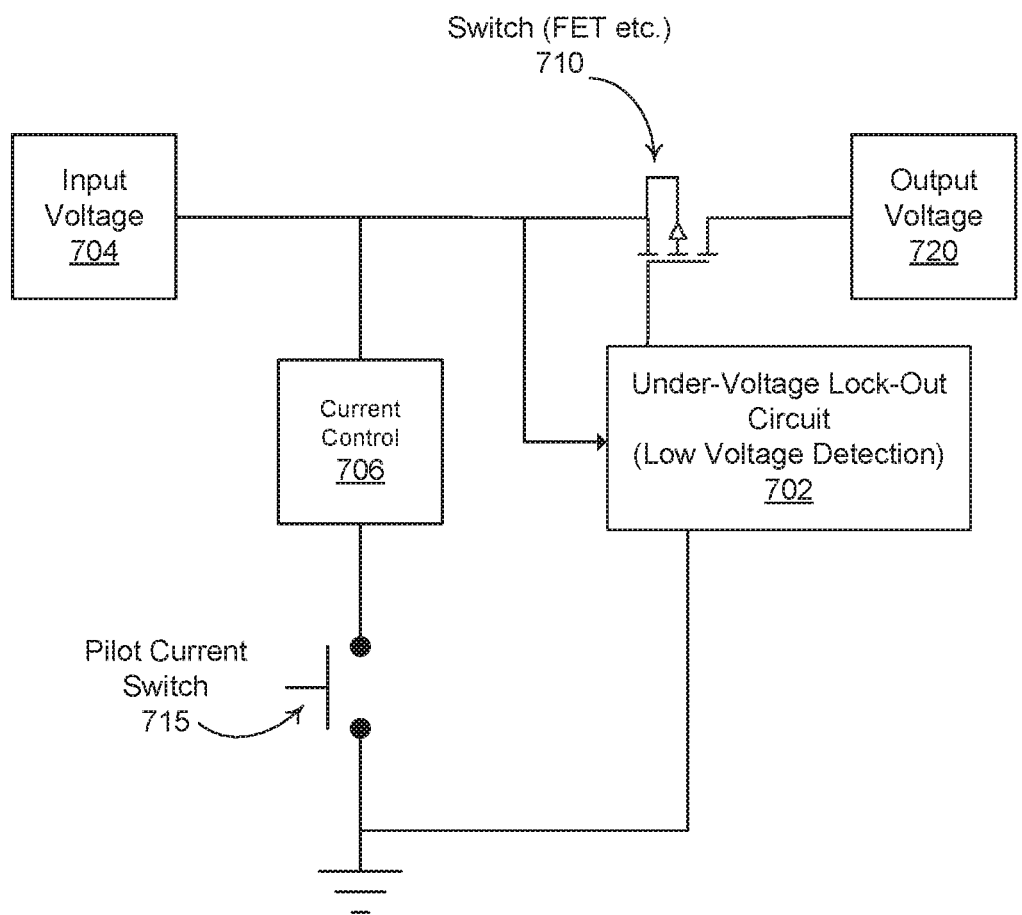
FIG. 7 shows an under-voltage lock-out circuit in accordance with one form of the present technology.

Voltages less than those which a component(s) is(are) designed to operate in may adversely affect or even damage the component(s). As the respiratory therapy device may receive a low voltage from the battery pack 102 while in 'stand-by' mode ("off"), the components within such a therapy or PAP device may receive low voltages, making certain components susceptible to damage. To block these low voltages from reaching the components of the respiratory therapy device, the respiratory therapy device may include an under-voltage lock-out circuit, as shown in FIG. 7. The under-voltage lockout circuit 702 may protect the respiratory therapy device from inadequate, low voltages. Further, the under-voltage lockout circuit may draw little to no power when the voltage provided from the battery pack and/or other power source is limited, such as below a predetermined threshold.

The under-voltage lock-out circuit 702 may, in some versions, include a transistor (e.g., inline P-channel MOSFET 710) and a first Zener diode. When the input voltage 704 of the power signal being delivered by the battery pack 102 to the under-voltage lock-out circuit 702 is below the first Zener diode's threshold voltage, no power will be provided to the circuits connected with the under-voltage lock-out circuit 702, such as the flow generator 404 or the PAP device 202. When the input voltage 704 exceeds the first Zener diode's threshold voltage plus the transistor's 710 threshold voltage, power supplied from the battery pack 102 may be passed to the circuits connected with the under-voltage lock-out circuit 702.

When powering on the respiratory therapy device from 'stand-by' mode, a fixed known resistance or constant current draw may be applied by the respiratory therapy device to the output power terminals of the stand-by voltage source. As such, the range of current drawn at output power terminals when a user attempts to turn on the respiratory therapy device may be known or predetermined. For example, the respiratory therapy device may include a button, such as power button or switch 230 in FIGS. 2A and 2B, which may provide a load that draws current from the stand-by voltage source in the required range or over the predetermined threshold. In some versions the button may also switch on the respiratory therapy device on when the stand-by circuit is in its 'on' state or when the respiratory therapy device is connected to an AC/DC adapter and not to a battery.

The respiratory therapy device may provide a controlled current draw from the stand-by voltage source by means of a momentary push switch or pilot current switch 715 in conjunction with a current control circuit. The momentary push switch or pilot current switch 715 may optionally, in some versions, be connected in series with the current control circuit 706 comprising a resistor and a second Zener diode. Upon activation of the momentary push switch or pilot current switch 715 (e.g., a user pushing the power button/switch 230), a current draw may result at the batteries output terminals. The pilot detect module may switch the system from 'stand-by' mode to an 'on' mode upon detection of a triggering event, such as upon detecting the current drawn from the stand-by voltage source surpassing a predetermined threshold and/or the current draw being maintained within the particular range for a predetermined amount of time. As previously described, while in 'on' mode the battery pack may provide the full output power signal, at an operating voltage, as well as a corresponding operating current, to the respiratory therapy device. This may be considered a dual-stage activation as discussed in more detail herein.

Figure 8:
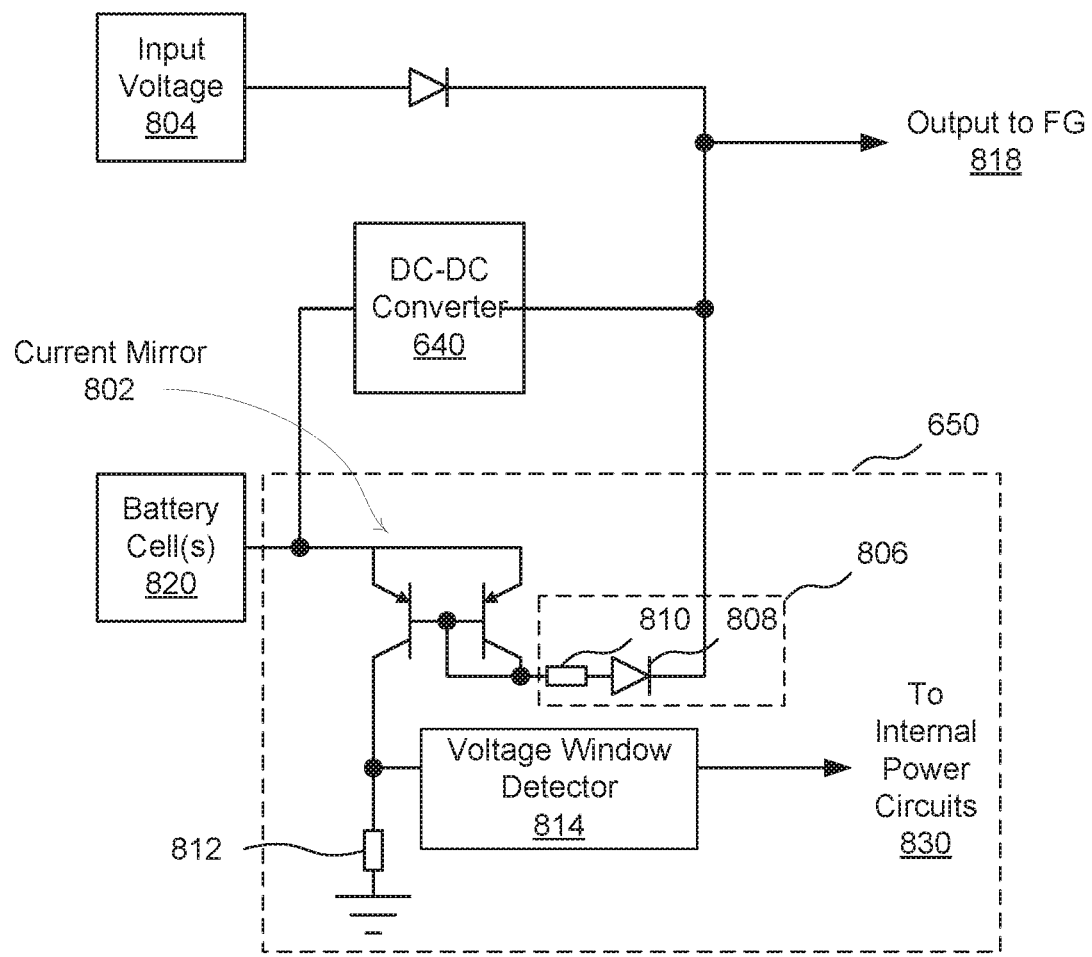
FIG. 8 shows a pilot detect module for a stand-by circuit in accordance with one form of the present technology.

Referring now to FIG. 8, the pilot detect module 650 may be implemented with a high side current mirror circuit powered directly from the cell(s) of the battery 820. In this regard, the high side current mirror circuit 802 may be implemented with a set of PNP transistors. In some embodiments other types of transistors or components may be used to implement the high side current mirror circuit. A reference leg, formed by diode 808 and resistor 810 may provide the PAP device with a high impedance, low voltage power signal at the output terminals. The high side current mirror is configured to allow the stand-by circuit to provide the pilot current at the output to the flow generator 818 of the PAP device 202 from the battery cell(s) 820 through reference leg 806.

The pilot detect module 650 may switch the power system from 'stand-by' mode to an 'on' mode, by performing the dual stage activation of the power system. In this regard, the high side current mirror circuit 802 mirrors the current sent through the reference leg 806. As such, the same current will also be output by the PNP transistors of the high side current mirror circuit 802 to the monitoring ICs of the circuit. In the first stage of the activation of the power system (e.g., in a "sleep state"), the mirrored current from the high side current mirror circuit 802 is provided to resistor 812 and detected as a voltage by integrated circuits of the voltage window detector 814 serving as a voltage monitor. This voltage is input into integrated circuits and monitored to determine if the voltage surpasses a predetermined threshold in the first stage. Upon the voltage window detector determining the voltage has surpassed the predetermined voltage threshold, the voltage window detector 814 may pass a low voltage internal power signal to the internal power circuits of the battery 102, as shown by element 830, thereby powering some components of the battery 102, such as the microcontroller, for the second stage (i.e., a transition to an "idle state").

The microcontroller may perform the second stage of the activation of the power system such as in an "idle state". In this regard, the microcontroller may instantiate a timer and begin tracking a time period during which the detected voltage surpasses the predetermined voltage threshold, or is within a particular range. Upon determining the detected voltage surpasses the predetermined voltage threshold for a certain or predetermined amount of time, such as by comparing the lapsed time of the timing period to a timing threshold, the microcontroller 670 may determine that the drawn current was in a range indicating the respiratory therapy device or PAP device is attempting to start up (e.g., from activation of momentary push switch or pilot current switch 715 previously described). Upon determining the PAP device is attempting to start up, the microcontroller may then activate the internal power circuits of the battery pack so as to power (enable) the operations of the battery pack (e.g., enable the DC/DC converter for voltage up-conversion from the battery/cells), thereby transitioning to a "supply state". Should the detected voltage not surpass the certain or predetermined amount of the time associated with the predetermined timing threshold, the microcontroller may instruct the pilot detect module 650 to power down the internal power circuits and refrain from powering up the PAP device, thereby transitioning (back) to the "sleep state" and turning off the microcontroller. By performing a two stage start up, the power system may be safer because it may help to ensure that non-intentional start-ups are avoided. In some embodiments activation of the power system may be blocked for a set duration of time after a false trigger of the pilot detect circuit is determined by the microcontroller 670.

Thus, in some versions, in the "stand-by" mode the DC-DC converter is not running. In this regard, the stand-by circuit may include a logic control connection between the microcontroller and the DC-DC converter and a switch, such as a mosfet switch, to control the DC-DC converter and its output. A signal disables the DC-DC converter and also blocks the output voltage from the DC-DC converter from reaching the output (when in standby mode). This may be a natural or default state of the signal and can require the microcontroller to actively de-assert this state to allow the DC-DC converter output. In the stand-by mode, the pilot voltage may be applied to the output (to the flow generator) and the battery may be activated by the flow generator drawing current from the pilot voltage. In this sense, the pilot source and pilot current detection components may also be part of the stand-by circuit.

6.5 Power States

The battery pack of the respiratory therapy device may operate in a plurality of power states. As shown in Table 1, below, the power states may include "sleep", "idle", "supply", "charge", and "UPS". The plurality of power states may be based on whether a power supply unit (PSU) is attached and/or active, whether a flow generator, such as flow generator 404 is in operation and/or attached, whether a user supplies an input requesting power from the battery, whether the battery has been powered off, etc.

Table 1, below, illustrates the characteristics of each power state of the battery including the conditions necessary for a given power state to occur and the resulting effect a given power state has on the operation of the battery. Similarly, FIG. 9 illustrates a state diagram outlining these characteristics.

are controlled by various inputs, including the microcontroller, pilot circuit, user interface button, and/or input power detection.

Thus, the battery may operate in an 'idle' power state 904 when a PSU and flow generator are disconnected from the battery, or not active. In the 'idle' power state the internal DC rails may be enabled and the microcontroller 670 may receive power. The charger components and power output may be disabled. Like the sleep' power state 902, the battery may operate a stand-by circuit as described above, when the battery is in an 'idle' power state.

Figure 9:
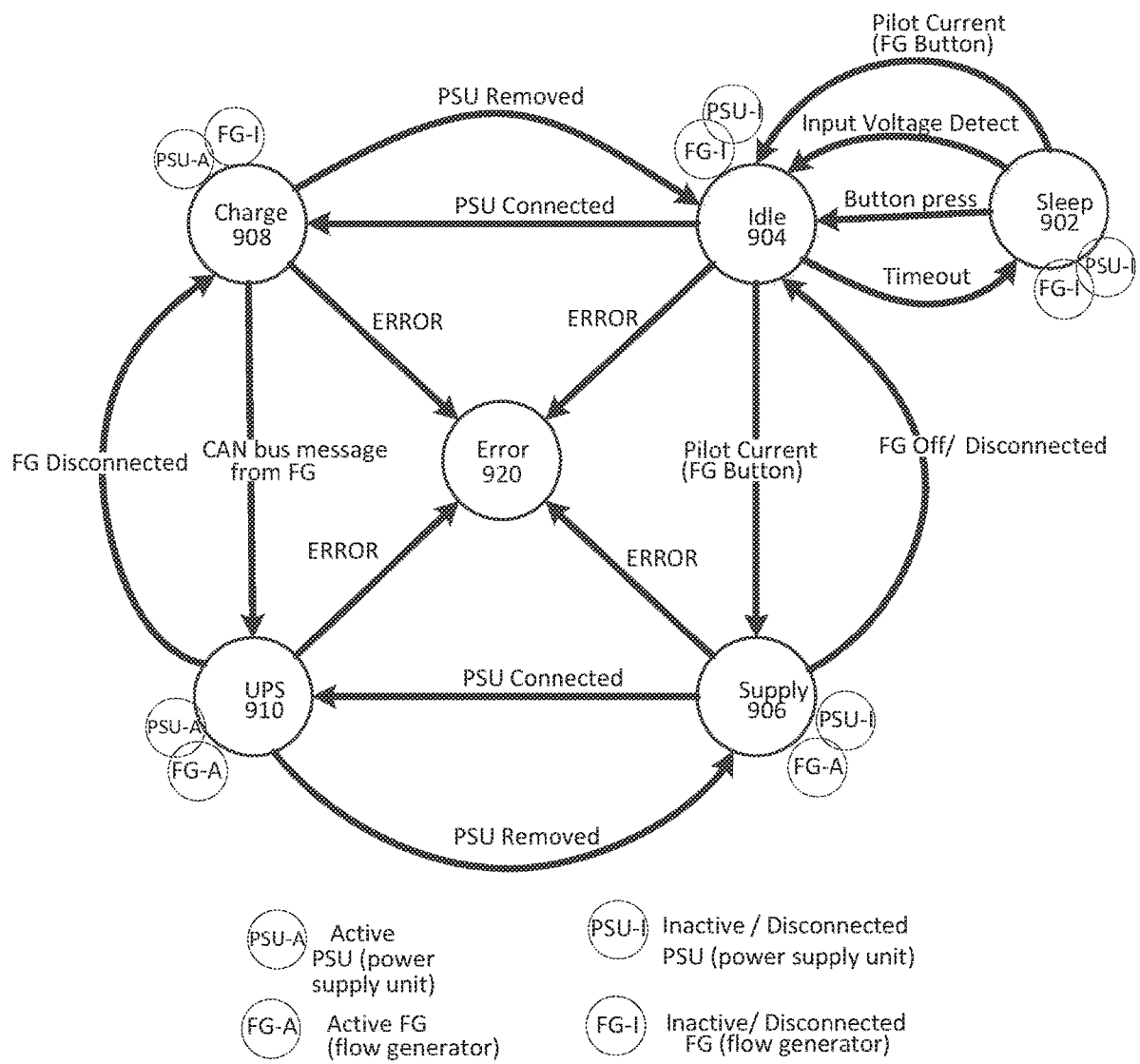
FIG. 9 shows state diagram of a battery in accordance with one form of the present technology.

The battery may also be in a 'supply' power state 906 when a PSU is disconnected from the battery, or not active, and a flow generator connected to the battery is active, as shown in FIG. 9. In the 'supply' power state the internal DC rails are enabled and the microcontroller 670 can operate. Additionally, full power output may be enabled but charging capabilities may be disabled.

The battery may also be in a 'charge' power state 908 when a PSU is connected to the battery and a flow generator is disconnected from the battery, or not active. In the 'charge' power state the internal DC rails may be enabled and the microcontroller may receive power and run one or more peripherals. Additionally, the charger components may

TABLE 1

| Mode | State | Active PSU Attached | Charger | DC-DC Converter Output | Micro-controller | Internal rails |
|---|---|---|---|---|---|---|
| Standby | sleep | No | Off | Off | Off | Off (or very low power) |
| Standby | Idle | No | Off | Off | On (Low Power) | On |
| Operating | Supply | No | Off | On(Full O/P) | On | On |
| Standby | Charge | Yes | On | Off | On | On |
| Operating | UPS | Yes | On | On (Low O/P & disconnected) | On | On |

As shown in FIG. 9, the battery may be in a 'sleep' power state 902 when a PSU is disconnected from the battery pack, or not active. In the 'sleep' power state, the internal rails, microcontroller 670, charger components, power systems 610, and power output may all be disabled.

In some versions of this 'sleep' power state 902, the battery may provide a stand-by voltage to its output terminals and provide power to the pilot detect module 650. As such, the battery may be able to detect input when a request to change power states is received, such as a button press of the power button/switch 230 by a user, as shown in FIG. 9, and as previously described. Similarly, the battery check button for activating the battery status indicator may operate on the stand-by power without activating the DC/DC converter for powering up to a levels necessary for the PAP device. When the battery check button is pressed, the device transitions to the idle state. Status is then displayed on the user interface in the idle state.

In the "Sleep" state, typically all the switchable internal power supplies may be turned off, and the microcontroller is not running. However, in the "idle" state, internal rails may be turned on (without turning on the DC-DC converter) and the microcontroller is running so that it can display status on the user interface and it can communicate externally on the CAN bus, and internally on the SMBus.

The "Sleep" and "Idle" states employ some latching circuits to enable/disable the internal power supplies, which be enabled and power output disabled, allowing the battery to charge while not being drained.

The battery may also be in an 'UPS' power state 910 when a PSU and flow generator are both connected and active. In the 'UPS' power state the internal DC rails and charger may be enabled. Further, the microcontroller may receive power and control peripherals. However, the power output or charging power, as measured in voltage, current, amps, or other such power output indicators, may be reduced, as the active PSU may supply the flow generator with the power necessary to operate.

The battery may be switched between power states as components are powered on and/or off, added, or removed, as shown in FIG. 9. For example, the battery may switch from the 'idle' state 904 to the 'charge' state 908 when a power supply unit attached to the battery is powered on. In another example, the battery may switch from the 'idle' state 904 to the 'supply' state 906 when the flow generator is powered on.

In some embodiments the battery may switch to an 'error' state 920. The error state may occur when the battery detects an abnormal operating parameter, such as too much power being drawn from the battery. Upon detecting an abnormal operating parameter, the battery may cease outputting power, shut down the internal rails, shut down charging operations, etc. As such, the battery may cease operations, or enter an 'idle' state, until the error is corrected. In some embodiments, the microcontroller may receive a small amount of power allowing the battery to output information to a user and/or to allow the battery to detect if the error condition has been corrected.

6.6 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A respiratory therapy device to generate a flow of breathable gas to a patient, comprising:
    a housing;
    a flow generator in the housing to generate the flow of breathable gas, the flow generator having an operating voltage; and
    a battery pack engageable with the housing, the battery pack configured to power the flow generator,
    wherein the battery pack includes a stand-by circuit and a microprocessor, the stand-by circuit and the microprocessor configured to perform a dual stage activation to switch the battery pack from a stand-by mode to an operating mode upon detecting a current drawn from the battery pack, the stand-by circuit comprising a voltage window detector for detecting a current demand of the flow generator while in the stand-by mode and a high side current mirror circuit for providing the current demand to the voltage window detector,
    wherein, at a first stage of the dual stage activation, the stand-by circuit is configured to detect whether the current drawn exceeds a predetermined threshold value, and after detecting that the current drawn exceeds the predetermined threshold value, the stand-by circuit is configured to pass an internal power signal to internal power circuits of the battery pack for powering the microprocessor for a second stage of the dual stage activation, and, at the second stage, the microprocessor is configured to detect whether the current drawn is maintained within a particular range for a predetermined period of time for switching to the operating mode.

2. The respiratory therapy device of claim 1 wherein the stand-by circuit is configured to provide a stand-by operations voltage while in the stand-by mode that is less than the operating voltage of the flow generator.

3. The respiratory therapy device of claim 2 wherein the stand-by circuit is configured to detect current demand of the flow generator with the stand-by operations voltage while in stand-by mode.

4. The respiratory therapy device of claim 3 wherein the flow generator further comprises a current control circuit and a switch, the current control circuit providing a controlled current draw upon activation of the switch.

5. The respiratory therapy device of claim 4 wherein the battery pack further includes a converter to convert a voltage of the battery pack to the operating voltage of the flow generator.

6. The respiratory therapy device of claim 5 wherein the microprocessor is configured to enable the converter after detection of the controlled current draw of the flow generator.

7. The respiratory therapy device of claim 5 wherein the converter is a direct current to direct current (DC/DC) converter configured to increase voltage of the battery pack to the operating voltage of the flow generator.

8. The respiratory therapy device of claim 5 wherein the microprocessor is configured to enable the converter after detection of the controlled current draw from the flow generator that exceeds the predetermined threshold value.

9. The respiratory therapy device of claim 5 wherein the microprocessor is configured to enable the converter after detection of the controlled current draw from the flow generator that exceeds the predetermined threshold value for the predetermined period of time.

10. The respiratory therapy device of claim 5 wherein the microprocessor is configured to:
   upon activation, determine whether the controlled current draw from the flow generator exceeds the predetermined threshold value for the predetermined period of time; and
   upon determining the controlled current draw exceeds the predetermined threshold value for the predetermined period of time, activate the converter for the operating mode.

11. The respiratory therapy device of claim 5 wherein the microprocessor is configured to:
   upon activation, determine whether the controlled current draw from the flow generator exceeds the predetermined threshold value for the predetermined period of time; and
   upon determining the controlled current draw does not exceed the predetermined threshold value for the predetermined period of time, trigger deactivation of the microprocessor.

12. The respiratory therapy device of claim 2 wherein the flow generator comprises an under-voltage lock-out circuit configured to disable the flow generator when the battery pack generates the stand-by operations voltage at an input to the under-voltage lock-out circuit.

13. The respiratory therapy device of claim 12 wherein the under-voltage lock-out circuit is configured to enable the flow generator when the battery pack generates a higher voltage than the stand-by operations voltage at the input to the under-voltage lock-out circuit.

14. The respiratory therapy device of claim 1 wherein the flow generator comprises a controller configured to control the flow generator to generate a positive airway pressure therapy.

15. A battery pack for a respiratory therapy device that generates a flow of breathable gas to a patient, the battery pack comprising;
   a battery housing for insertion into a flow generator housing;
   a cell within the battery housing for producing a voltage;
   a converter to convert the voltage from the cell to an operating voltage for the respiratory therapy device;
   an output connector of the battery pack configured to provide the operating voltage to an input connector of the flow generator; and
   a stand-by circuit and a microprocessor, the stand-by circuit and the microprocessor configured to perform a dual stage activation to switch the battery pack from a stand-by mode to an operating mode of the battery pack upon detection of a current drawn from the battery pack, the stand-by circuit comprising a voltage window detector for detecting a current demand of the flow generator while in the stand-by mode and a high side current mirror circuit for providing the current demand to the voltage window detector,
   wherein, at a first stage of the dual stage activation, the stand-by circuit is configured to detect whether the current drawn exceeds a predetermined threshold value, and after detecting that the current drawn exceeds the predetermined threshold value, the stand-by circuit is configured to pass an internal power signal to internal power circuits of the battery pack for powering the microprocessor for a second stage of the dual stage activation, and, at the second stage, the microprocessor is configured to detect whether the current drawn is maintained within a particular range for a predetermined period of time for switching to the operating mode.

16. The battery pack of claim 15 wherein the stand-by circuit is configured in the stand-by mode to provide a stand-by operations voltage to the output connector that is less than the operating voltage of the flow generator.

17. The battery pack of claim 16 wherein the stand-by circuit is configured in the stand-by mode to detect current demand of the flow generator at the output connector with the stand-by operations voltage.

18. The battery pack of claim 16 wherein the stand-by circuit is configured to disable the converter in the stand-by mode.

19. The battery pack of claim 16 wherein the microprocessor is configured to enable the converter after detection of a controlled current at the output connector of the flow generator with the stand-by operations voltage.

20. The battery pack of claim 15 wherein the converter is a direct current to direct current (DC/DC) converter configured to increase the voltage of the battery pack to the operating voltage of the flow generator.

21. The battery pack of claim 15 wherein the microprocessor is configured to enable the converter after detection of a controlled current at the output connector that exceeds the predetermined threshold value.

22. The battery pack of claim 15 wherein the microprocessor is configured to enable the converter after detection of a controlled current at the output connector that exceeds the predetermined threshold value for the predetermined period of time.

23. A respiratory therapy device to generate a flow of breathable gas to a patient, comprising:
   a housing;
   a flow generator in the housing to generate the flow of breathable gas, the flow generator having an operating voltage; and
   a battery pack engageable with the housing, the battery pack configured to power the flow generator,
   wherein the battery pack includes a stand-by circuit and a microprocessor, the stand-by circuit and the microprocessor configured to perform a dual stage activation to switch the battery pack from a stand-by mode to an operating mode upon detecting a current drawn from the battery pack, the stand-by circuit comprising a voltage window detector for detecting a current demand of the flow generator while in the stand-by mode and a high side current mirror circuit for providing the current demand to the voltage window detector, wherein, at a first stage of the dual stage activation, the stand-by circuit is configured to detect whether the current drawn exceeds a predetermined threshold value, and after detecting that the current drawn exceeds the predetermined threshold value, the stand-by circuit is configured to pass an internal power signal to internal power circuits of the battery pack for powering the microprocessor for second stage of the dual stage activation, and, at the second stage, the microprocessor is configured to detect whether the current drawn is maintained within a particular range for a predetermined period of time for switching to the operating mode, wherein the stand-by circuit is configured to, while in the stand-by mode, detect current demand of the flow generator with a stand-by operations voltage that is less than the operating voltage of the flow generator.

24. The respiratory therapy device of claim 23 wherein the flow generator further comprises a current control circuit and a switch, the current control circuit providing a controlled current draw upon activation of the switch.

25. The respiratory therapy device of claim 24 wherein the battery pack further includes a converter to convert a voltage of the battery pack to the operating voltage of the flow generator.

26. The respiratory therapy device of claim 25 wherein the microprocessor is configured to enable the converter after detection of the controlled current draw of the flow generator.

27. The respiratory therapy device of claim 25 wherein the converter is a direct current to direct current (DC/DC) converter configured to increase voltage of the battery pack to the operating voltage of the flow generator.

28. The respiratory therapy device of claim 25 wherein the microprocessor is configured to enable the converter after detection of the controlled current draw from the flow generator that exceeds the predetermined threshold value.

29. The respiratory therapy device of claim 23 wherein the flow generator comprises an under-voltage lock-out circuit configured to disable the flow generator when the battery pack generates the stand-by operations voltage at an input to the under-voltage lock-out circuit.

30. The respiratory therapy device of claim 23 wherein the flow generator comprises a controller configured to control the flow generator to generate a positive airway pressure therapy.

* * * * *